(12) United States Patent
Baird

(10) Patent No.: US 9,402,617 B2
(45) Date of Patent: Aug. 2, 2016

(54) SUTURE ANCHORS AND METHODS OF USE

(71) Applicant: Kevin N. Baird, Phoenix, AZ (US)

(72) Inventor: Kevin N. Baird, Phoenix, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 225 days.

(21) Appl. No.: 13/573,791

(22) Filed: Oct. 3, 2012

(65) Prior Publication Data

US 2013/0103083 A1      Apr. 25, 2013

Related U.S. Application Data

(60) Provisional application No. 61/542,688, filed on Oct. 3, 2011.

(51) Int. Cl.
*A61B 17/04* (2006.01)

(52) U.S. Cl.
CPC ..... *A61B 17/0401* (2013.01); *A61B 2017/0409* (2013.01); *A61B 2017/0412* (2013.01); *A61B 2017/0414* (2013.01); *A61B 2017/0438* (2013.01); *A61B 2017/0445* (2013.01)

(58) Field of Classification Search
CPC .................. A61B 17/0401; A61B 2017/0445; A61B 2017/00004
USPC ........................................... 606/72, 232, 301
See application file for complete search history.

(56) References Cited

U.S. PATENT DOCUMENTS

| | | | |
|---|---|---|---|
| 5,690,676 A | 11/1997 | Dipoto | |
| 5,733,307 A | 3/1998 | Dinsdale | |
| 5,980,558 A | 11/1999 | Wiley | |
| 6,045,574 A | 4/2000 | Thal | |
| 6,183,479 B1 | 2/2001 | Tormala et al. | |
| 6,508,830 B2 | 1/2003 | Steiner | |
| 6,524,317 B1 | 2/2003 | Ritchart et al. | |
| 6,527,794 B1 | 3/2003 | McDevitt et al. | |
| 6,692,516 B2 | 2/2004 | West, Jr. et al. | |
| 6,855,157 B2 | 2/2005 | Foerster et al. | |

(Continued)

FOREIGN PATENT DOCUMENTS

| | | |
|---|---|---|
| WO | 2006044491 A2 | 4/2006 |
| WO | 2009055800 A1 | 4/2009 |

(Continued)

OTHER PUBLICATIONS

International Search Report and Written Opinion, corresponding to PCT/US2012/000493, International filing date Oct. 3, 2012.

(Continued)

*Primary Examiner* — Victor Nguyen

(74) *Attorney, Agent, or Firm* — Donald E. Stout; Stout, Uxa & Buyan, LLP

(57) ABSTRACT

An anchoring system for securing tissue to bone includes an implant having a body through which a suture eyelet extends transversely, a suture recess extending along a portion of a length of the body, having a predetermined depth below an outer surface of the body, and a suture pinch ramp disposed at a proximal end of the suture recess. The suture pinch ramp has a depth approximately equal to the predetermined depth at a distal end thereof and sloping outwardly in a proximal direction so that a depth of a proximal end of the suture pinch ramp approaches zero. An insertion member includes an insertion tube and a handle which is engageable with the anchor body to deploy the anchor in a selected bone site.

11 Claims, 11 Drawing Sheets

(56) References Cited

U.S. PATENT DOCUMENTS

| | | |
|---|---|---|
| 7,037,324 B2 | 5/2006 | Martinek |
| 7,217,279 B2 | 5/2007 | Reese |
| 7,235,100 B2 | 6/2007 | Martinek |
| 7,320,701 B2 | 1/2008 | Haut et al. |
| 7,572,275 B2 | 8/2009 | Fallin et al. |
| 7,585,311 B2 | 9/2009 | Green et al. |
| 7,588,587 B2 | 9/2009 | Barbieri et al. |
| 8,414,613 B2* | 4/2013 | Huxel et al. .................. 606/232 |
| 2004/0098052 A1 | 5/2004 | West, Jr. et al. |
| 2004/0138706 A1 | 7/2004 | Abrams |
| 2006/0271060 A1 | 11/2006 | Gordon |
| 2007/0203498 A1 | 8/2007 | Gerber et al. |
| 2008/0009904 A1 | 1/2008 | Bourque et al. |
| 2008/0103528 A1 | 5/2008 | Zirps et al. |
| 2009/0076544 A1 | 3/2009 | DiMatteo et al. |
| 2009/0082807 A1 | 3/2009 | Miller et al. |
| 2009/0234387 A1 | 9/2009 | Miller et al. |
| 2009/0248068 A1* | 10/2009 | Lombardo et al. ............ 606/232 |
| 2010/0016869 A1 | 1/2010 | Paulk et al. |
| 2010/0198258 A1* | 8/2010 | Heaven et al. ................ 606/232 |
| 2011/0152929 A1 | 6/2011 | McDevitt et al. |

FOREIGN PATENT DOCUMENTS

| | | |
|---|---|---|
| WO | 2010-101638 A1 | 9/2010 |
| WO | 2012037699 A1 | 3/2012 |

OTHER PUBLICATIONS

Japan Patent Office Office Action issued Nov. 4, 2015 (English Translation received Jan. 22, 2016) in connection with corresponding Japan App. No. 2014-534549.

EPO Search Report issued Mar. 27, 2015 in connection with corresponding EPO App. No. 12838797.4.

* cited by examiner

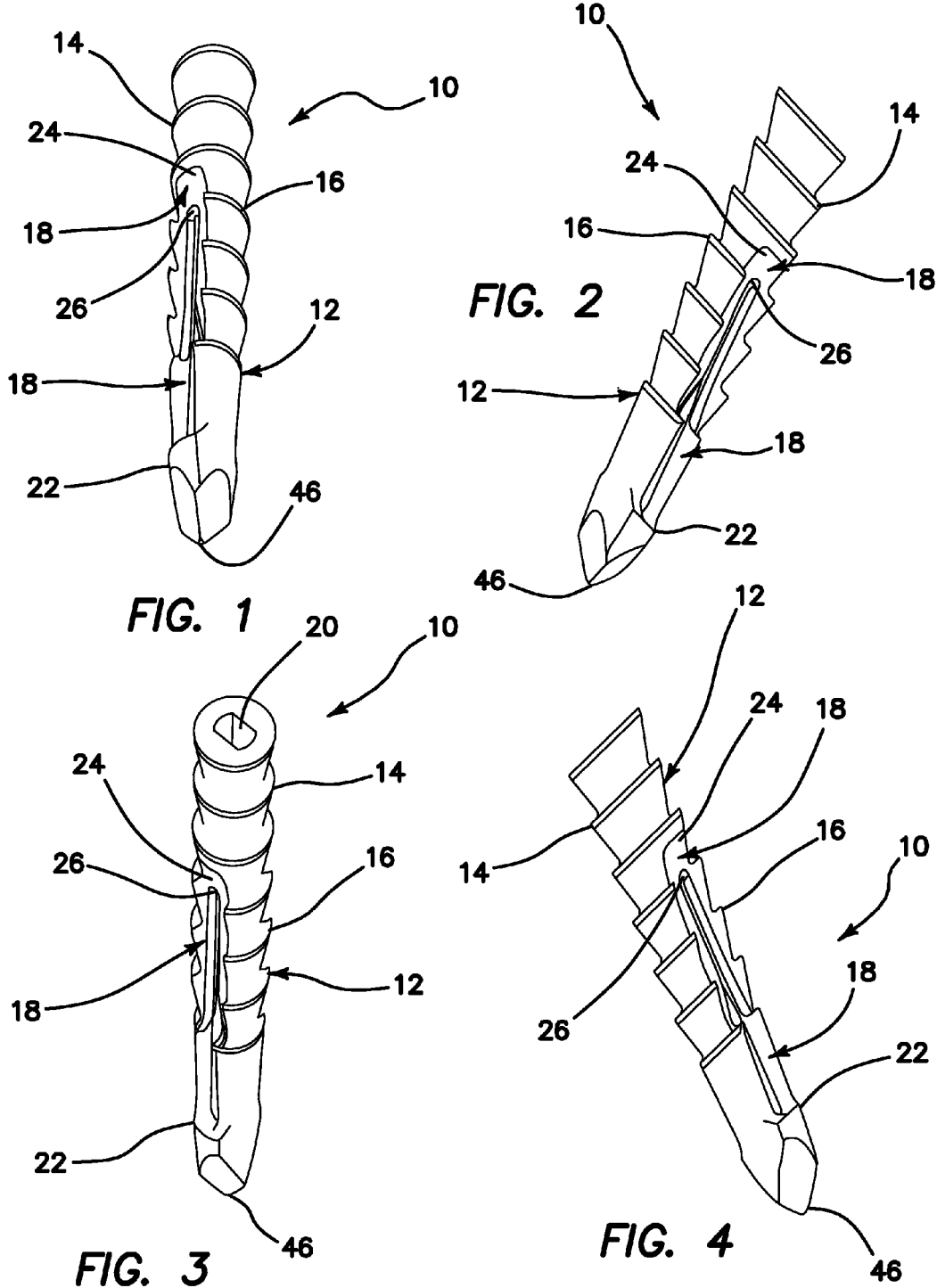

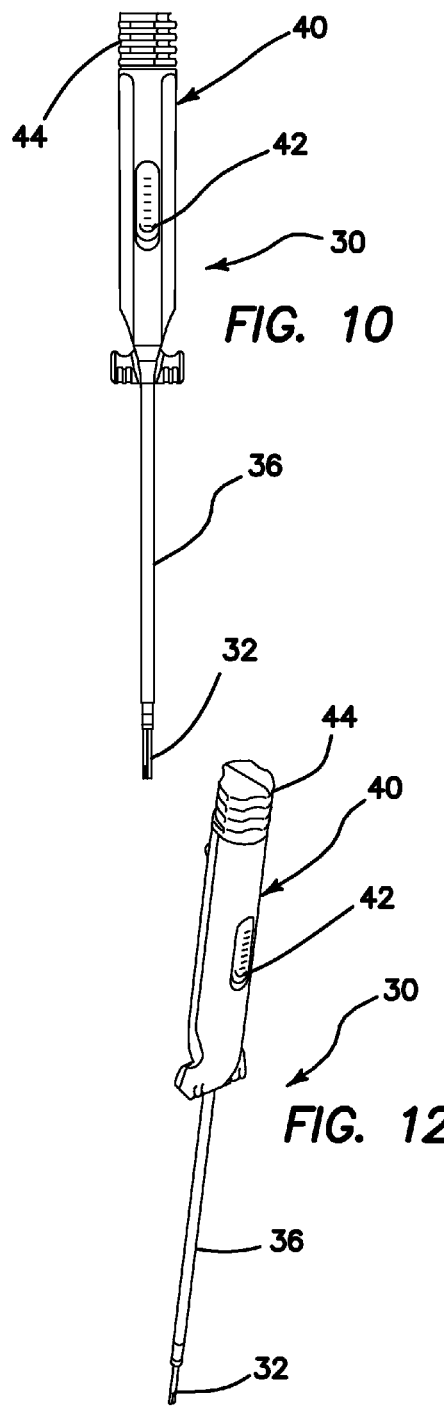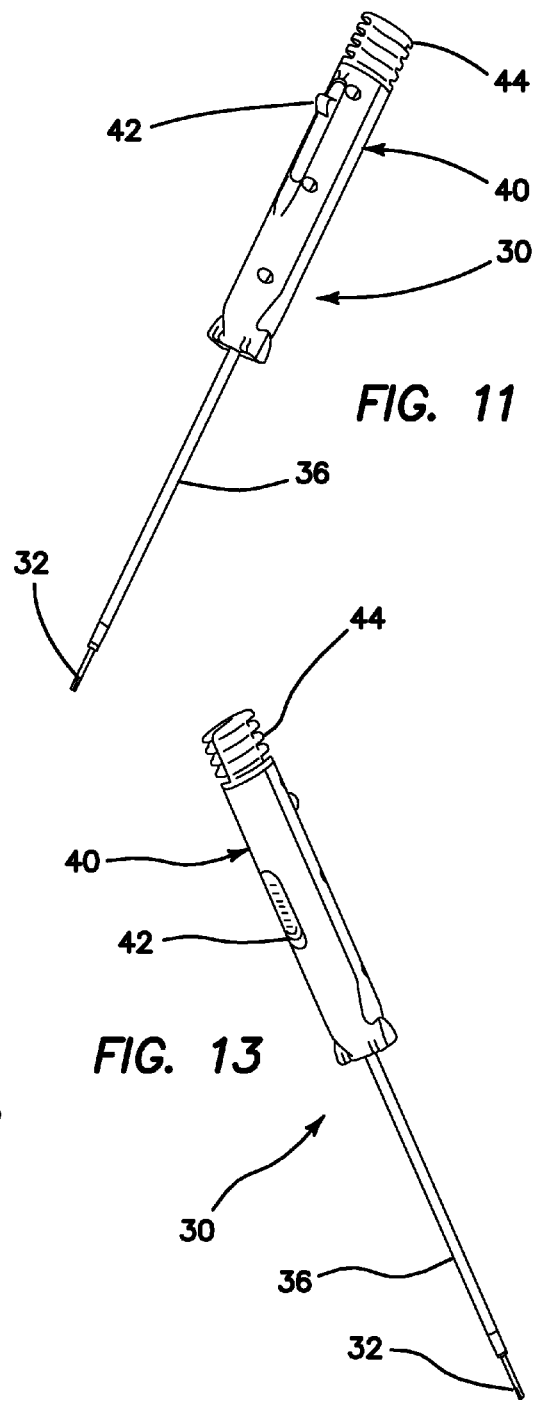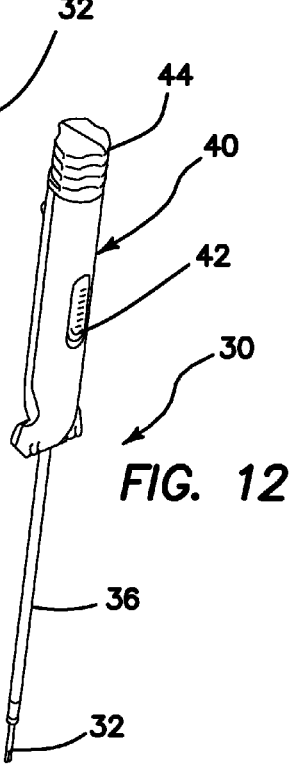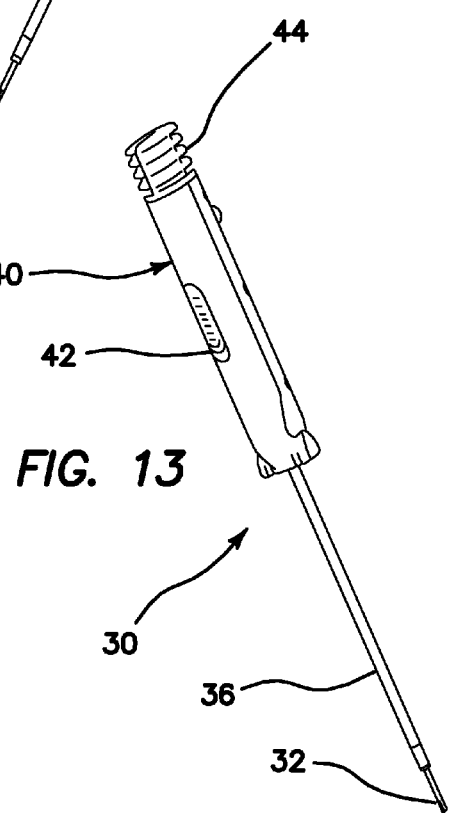
FIG. 10
FIG. 11
FIG. 12
FIG. 13

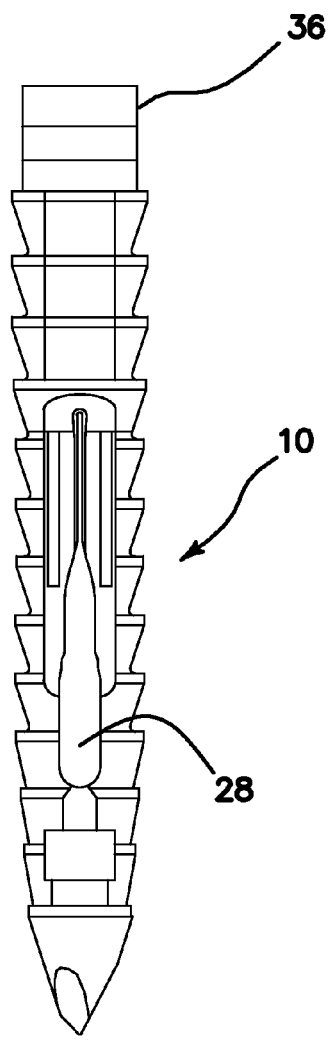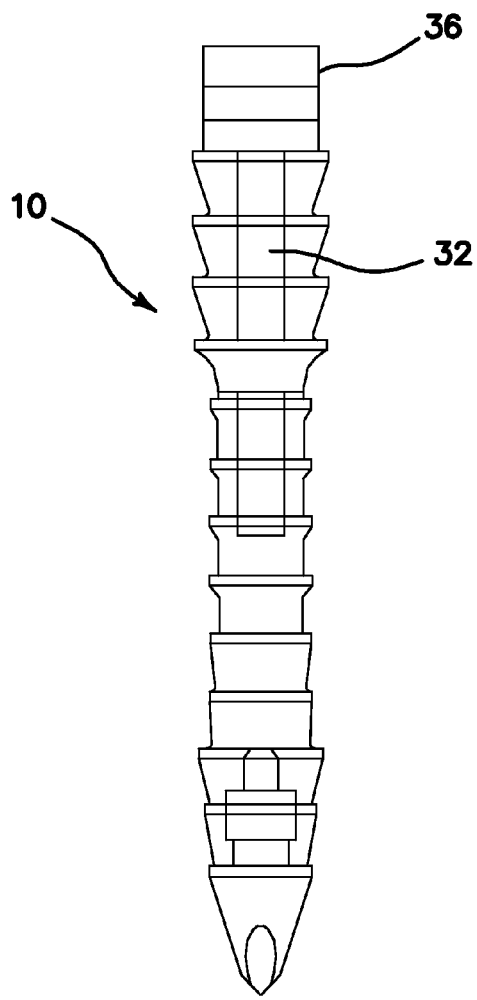
FIG. 26
FIG. 27

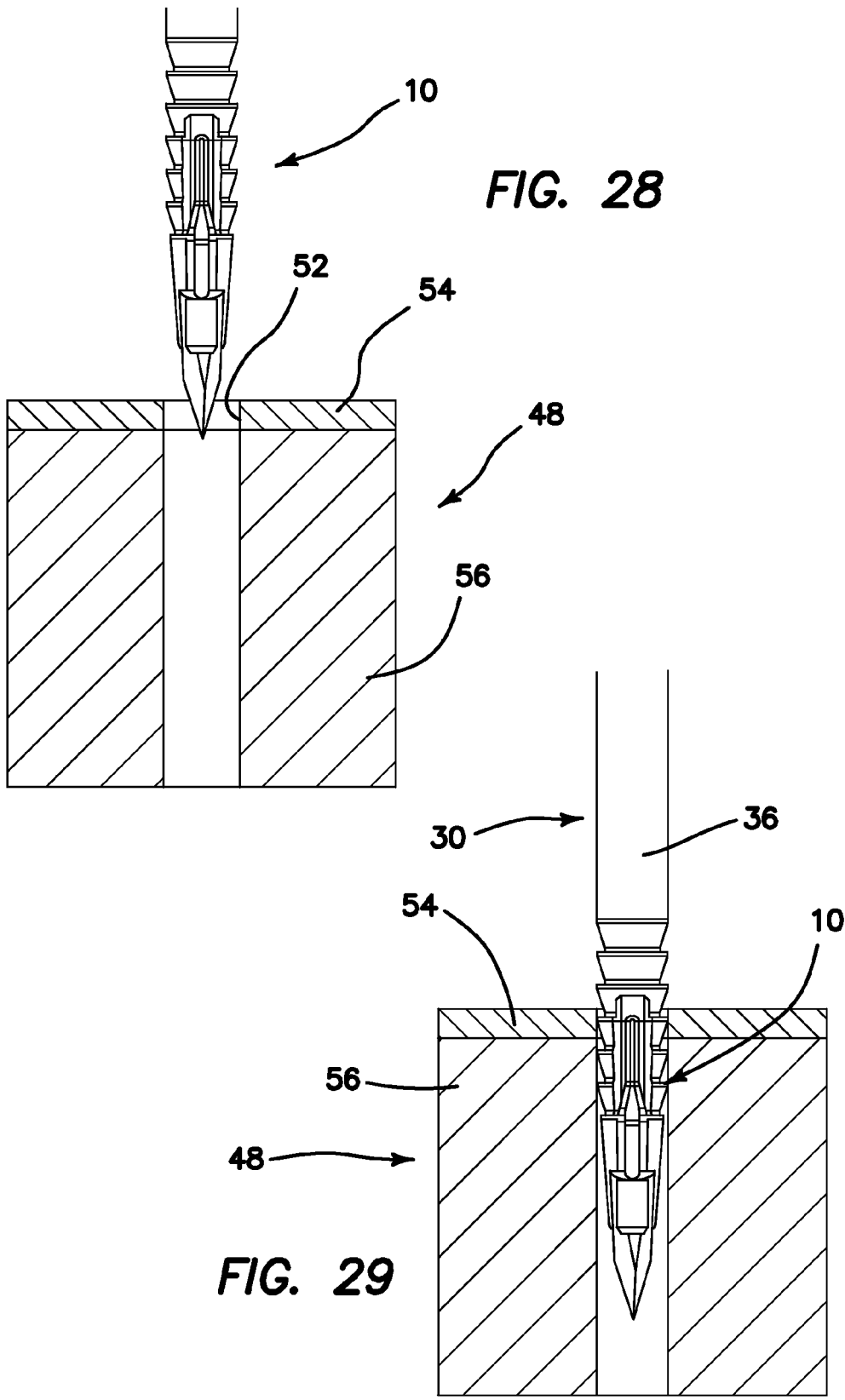

SUTURE ANCHORS AND METHODS OF USE

This application claims the benefit under 35 U.S.C. 119(e) of the filing date of Provisional U.S. Application Ser. No. 61/542,688, entitled Suture Anchor, filed on Oct. 3, 2011, which application is herein expressly incorporated by reference, in its entirety.

BACKGROUND OF THE INVENTION

There are many suture anchor designs on the market today which are intended to secure suture, wherein the suture is passed through soft tissue to bone. Preferred methods often use anchors that do not require placing knots in the suture to secure the tissue to the anchor. This shift has allowed for a simpler, less time consuming procedure. Also, the knots have been shown to be a common source of anchor failure.

However, the knotless anchors have many challenges. Many anchors can change the tension in the suture during deployment, which requires the surgeon to estimate how much tension will be added during the final installation step. This can result in under- or over-tensioning of the tissue against the bone. Anchors that allow the suture to be tensioned after the anchor is implanted can be complicated, with many components which lead to expensive and unreliable anchors. These types of anchors can have user-assisted tensioning devices that can lead to over-tensioned suture that have the ability to pull the anchor out of the bone.

Other anchors that allow the suture to be tensioned prior to implanting the anchor can leave the sutures with uneven tension. Also, many of the anchors are unable to utilize more than two suture ends and have undesirable metal components.

There have been many different anchors used t secure suture to bone. As described above, the knotless anchor designs are preferred due to knot failures.

The PUSHLOCK™ anchor, marketed by Arthrex, is a two-part anchor. The tip of the anchor has an eyelet through which the suture legs are loaded. This tip is placed at the bottom of a hole drilled into the bone. At this point, the surgeon may adjust the tension on the suture, thereby pulling the tissue closer to the surface of the bone. Since the suture is tensioned all at once, without any engagement with the hole when the rear portion of the anchor is driven into the hole, the tension may not be correct. Once the rear portion of the anchor is in the hole, the suture tension cannot be adjusted.

Smith and Nephew market the KINSA™ suture anchor. This anchor is a knotless design made of PEEK (polyether ether ketone) which is tapped into a pre-drilled hole in the bone. The anchor is preloaded with suture tied in a one-way sliding knot within the anchor body, which allows the surgeon to adjust the tension after the anchor has been deployed. This cannot utilize suture that is already passed through tissue and only can provide a simple stitch in the tissue.

The POPLOK™ by Conmed Linvatec is another knotless anchor. It is a two piece polymer anchor that has the ability of accepting and tensioning the suture individually prior to locking the suture to the anchor. However, the anchor has multiple pieces that can fail.

The VERSALOK™ by Mitek is also a knotless anchor. It is a two piece polymer and metal design that has the ability of accepting and tensioning the suture individually prior to locking the suture to the anchor. It does have multiple parts forming the anchor and the inner member is metallic.

The CUFFLINK™ Knotless and CUFFLINK SP™ Knotless suture (self punching with metal tip) anchors, also marketed by Mitek, are fabricated of PEEK, using a one-piece polymer design without the employment of any metal. The design allows the anchor to accept more than two suture ends, and each of these ends can be tensioned or have tension released individually by hand, prior to final anchor deployment, providing the surgeon the ability to achieve the desired tension on each suture. The anchor may also accept tissue (such as a tendon, ligament, zenograft, allograft, or collagen scaffold) with or without suture, enabling a direct tissue to bone repair. The metal tip version allows the anchor to be malleted directly into the bone without the need for a pilot hole. Finally, the design incorporates a metal deployment device to provide strength to the anchor during deployment, thereby reducing breaking of the anchor.

SUMMARY OF THE INVENTION

The present invention provides a suture or tissue anchor which is intended to secure suture or tissue to bone. There are many soft tissue to bone repair procedures, such as rotator cuff, SLAP (Superior Labral tear from Anterior to Posterior), and Bankart lesion repairs, or reconstruction of labral tissue to the glenoid rim, in which a surgeon needs to secure tissue in close contact with bone. Often the bone surface is roughened, and when tissue is pulled into intimate contact, the body's healing response will fuse the tissue and bone together. This suture is then passed through the soft tissue at the desired location, and the suture is secured to the anchor by tying a knot. Other methods include passing suture through the tissue first and then fastening the anchor and suture to the bone without knots.

More particularly, there is provided in one aspect of the present invention an anchoring system for securing tissue to bone, which comprises an implant having a body which includes a suture eyelet extending transversely therethrough, a suture recess extending along a portion of a length of the body, having a predetermined depth below an outer surface of the body; and a suture pinch ramp disposed at a proximal end of the suture recess. The suture pinch ramp has a depth approximately equal to the predetermined depth at a distal end thereof and sloping outwardly in a proximal direction so that a depth of a proximal end of the suture pinch ramp approaches zero.

Preferably, the implant further comprises external surface features for securing the implant within surrounding bone. These external surface features comprise bone barbs. Suture barbs are disposed on the outer surface of the body at a proximal end thereof, for clamping suture or tissue between the outer surface of the body and adjacent bone. Bone displacement tabs are disposed on a distal portion of the implant body, for displacing bone distal to suture for allowing optimal suture sliding during initial deployment of the anchor.

An inner cavity is provided in the anchor body, having an opening at a proximal end of the anchor body for receiving an insertion device. The anchoring body further comprises a suture cleat adjacent to the suture pinch ramp.

The anchoring system further comprises an insertion member which is engageable with the anchor body to deploy the anchor in bone. The insertion member comprises a proximal handle portion and an insertion tube connected to a distal end of the handle portion. A suture pulley rod is extendable from and retractable into a distal end of the insertion tube. A pair of cleat retainers are provided on a distal end of the pulley rod, wherein a gap is disposed between the pair of cleat retainers. A rotatable knob is disposed on the handle portion for retracting and extending the pulley rod relative to the insertion tube. A knob release slide disposed on the handle.

In another aspect of the invention, there is disclosed a method for securing soft tissue to bone, which comprises steps of driving an implantable anchor having a body distally into a desired bone site, using an insertion device, to a predetermined initial deployment depth, and applying pressure to suture or tissue disposed between the anchor body and adjacent bone, using a recess disposed on an outer surface of the body and a pinch ramp also disposed on the outer surface of the body, proximal to the suture recess. Additional steps include tensioning free ends of the suture or tissue disposed between the anchor body and adjacent bone to a desired level, withdrawing a pulley rod proximally into an insertion tube comprising a portion of the insertion device, and driving the implantable anchor a further distance distally into the bone site to finally deploy the anchor. The suture or tissue is pinched between barbs on an outer surface of the implant body and adjacent bone and also between cleats on both sides of the anchor body to lock the suture or tissue in place. Further inventive method steps include withdrawing the pulley rod from the anchor body and releasing the insertion device therefrom; and trimming the free suture ends to complete the procedure.

In still another aspect of the invention, there is provided an anchoring system for securing tissue to bone, which comprises an insertion member which is engageable with an anchor body to deploy the anchor body in bone. The insertion member comprises a proximal handle portion, an insertion tube connected to a distal end of the handle portion, and a suture pulley rod extendable from and retractable into a distal end of the insertion tube. A pair of cleat retainers are disposed on a distal end of the pulley rod, wherein a gap is disposed between the pair of cleat retainers. A rotatable knob is provided on the handle portion for retracting and extending the pulley rod relative to the insertion tube, and a knob release slide is disposed on the handle.

The invention, together with additional features and advantages thereof, may best be understood by reference to the following description taken in conjunction with the accompanying illustrative drawing.

BRIEF DESCRIPTION OF THE DRAWINGS

FIGS. 1-4 are isometric views of an implantable anchor constructed in accordance with the principles of the present invention, illustrating the anchor from four different perspectives;

FIGS. 10-13 are isometric views illustrating the insertion system of the present invention, including the handle portion;

FIG. 26 is an elevational view of the anchor of the present invention showing a step which is performed prior to final deployment of the anchor;

FIG. 27 is an elevational view similar to FIG. 26, showing the illustrated step from a different orientation;

FIG. 28 is an elevational view illustrating the first step of the inventive method which is also shown in FIGS. 14-17, with the suture removed for clarity;

FIG. 29 is an elevational view similar to FIG. 28, illustrating the second step of the inventive method which is also shown in FIGS. 18-21, with the suture removed for clarity;

DESCRIPTION OF THE PREFERRED EMBODIMENT

Figure 5:
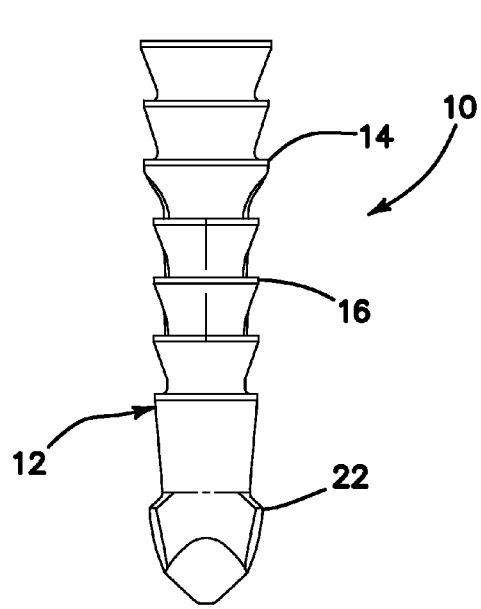
FIG. 5 is an elevational view of the anchor of FIGS. 1-4.
Figure 6:
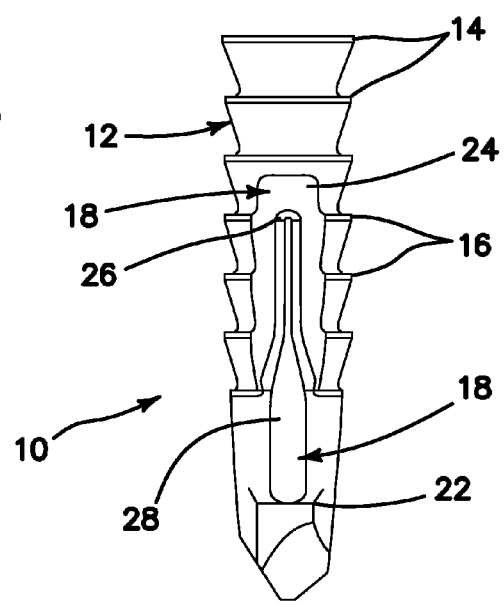
FIG. 6 is an elevational view similar to FIG. 5, from an opposed orientation.
Figure 7:
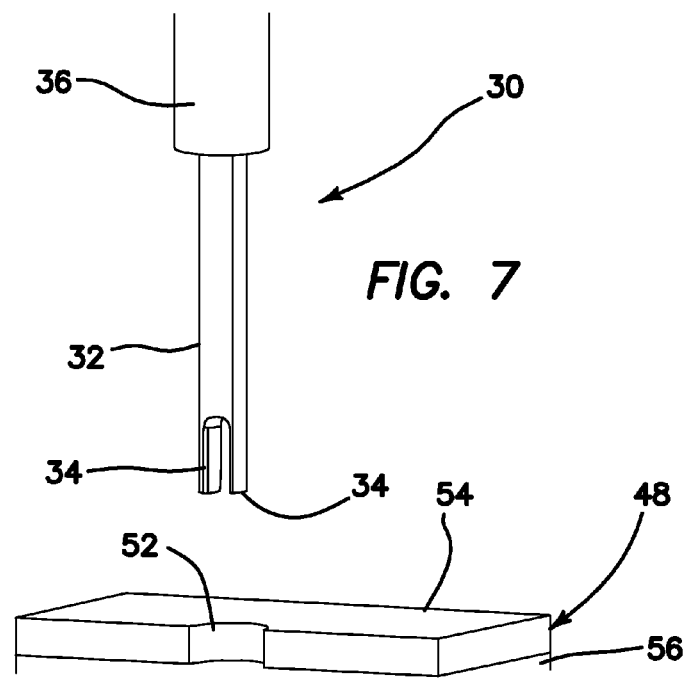
FIG. 7 is an isometric view of the insertion system of the present invention.
Figure 8:
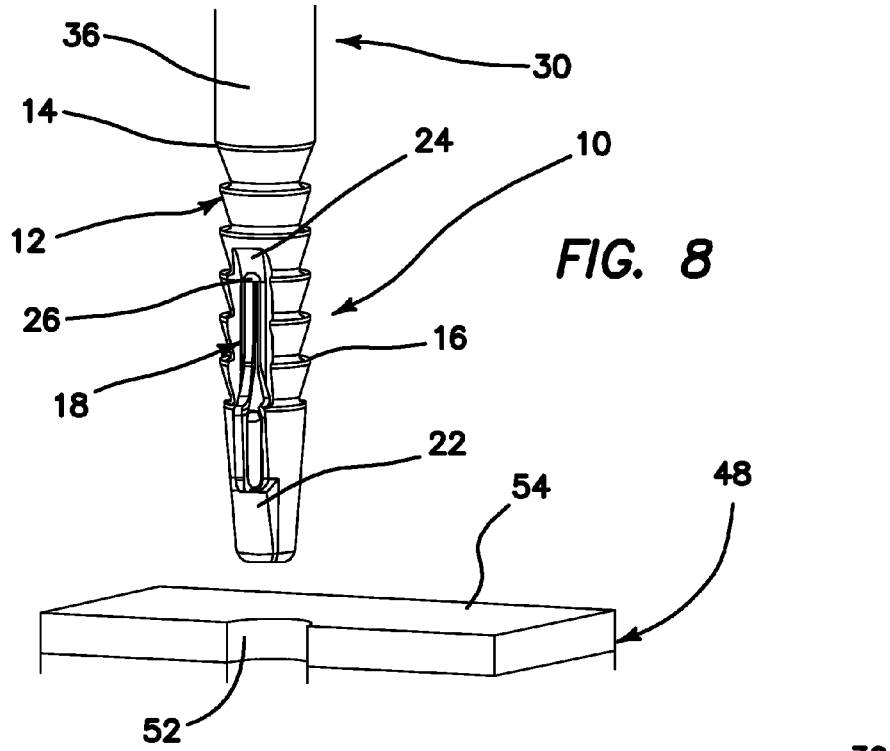
FIG. 8 is an isometric view similar to FIG. 7 illustrating the assembled insertion system and anchor of the present invention in position to be deployed.

The inventive system and methods disclosed herein comprise a simple-to-insert suture anchor which allows adjustment of suture or tissue tension prior to deployment, does not change the tension on the suture or tissue (and as a result, the captured tissue) when it is deployed, does not require a knot to secure the suture or tissue, and accepts multiple suture ends.

Referring now more particularly to the drawings, there is shown in FIGS. 1-6 a suture anchor 10 constructed in accordance with the principles of the present invention. The anchor 10 comprises a body 12 having a plurality of proximal suture barbs 14, as well as bone barbs 16. A portion of the outer surface of the body 12 comprises a suture recess 18. An inner cavity 20 (FIG. 3) is provided for accommodating a suture pulley rod, to be described below. The distal end of the anchor body 12 includes bone displacement tabs 22.

Within the suture recess 18 are disposed a suture pinch ramp 24, a suture cleat 26, and a suture eyelet 28, which extends transversely through a width of the body 12 so that it is open to opposing sides of the body.

Now with reference to FIGS. 7-13, the insertion system 30 for the anchor 10 will be described. The insertion system or inserter 30 comprises a suture pulley rod 32 (FIG. 7), suture cleat retainers 34 on the distal end of the pulley rod 32 (also FIG. 7), and an insertion tube 36. In some embodiments, an optional metal distal tip 38 (FIG. 9) may be employed.

A handle portion 40 of the insertion system 30 is illustrated in FIGS. 10-13. The handle portion 40 comprises a knob release slide 42 and a proximal knob 44.

The anchor 10 has a number of features that are important to its innovative function. For example, the suture barbs 14 pinch the suture against the surrounding bone when the implant is deployed. The remaining barbs are the bone barbs 16, distal to the suture barbs 14, function to engage the bone during the initial and final deployment. The suture recess 18, because of its recessed profile relative to remaining portions of the outer surface of the body 12, allows the suture to slide between the anchor body and adjacent bone during the initial deployment. The inner cavity 20 for the suture pulley rod 32, allows for the metal suture pulley rod 32 to support the anchor during initial deployment. The bone displacement tabs 22 displace the bone distal to the suture to allow for optimal suture sliding during initial deployment.

Figure 9:
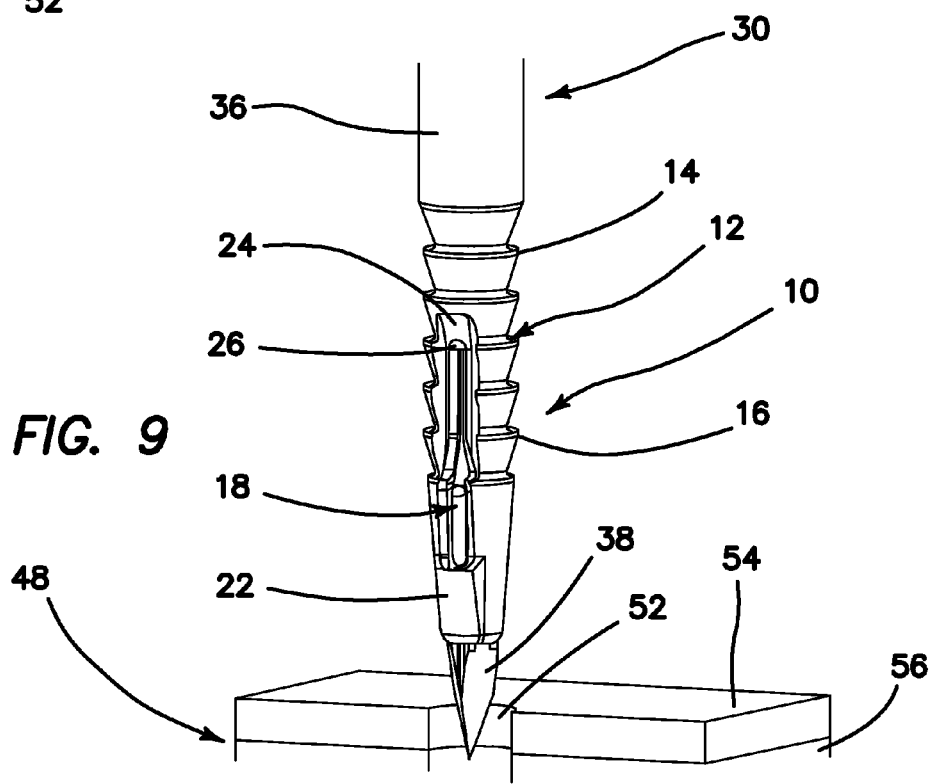
FIG. 9 is an isometric view similar to FIG. 8, wherein the assembly is being inserted into a desired bone location.

The suture pinch ramp 24 helps to maintain tension during individual tensioning of the suture. It is configured to slope outwardly in a proximal direction, so that its distal end is at a depth approximating the depth of the suture recess 18 and its proximal end is at the outer surface of the implant body 12, i.e. a depth of approximately zero. The suture cleat 26 pinches the suture to increase the suture pullout strength of the construct. The suture eyelet 28 allows for one or more suture ends to be placed in the implant. Each suture end is individually tensionable, as well be described below. Though the tip 46 of the anchor 10 is illustrated as being closed, as shown in FIG. 9, the optional metal tip 38 may be added to the anchor 10 to allow for the anchor to be inserted directly into bone without the requirement of a pilot hole.

The insertion system 30, as well, has several important features which contribute to the innovative function of Applicant's inventive system. In particular, the suture pulley rod 32, in the initial deployment stage, allows the suture to move freely in the suture eyelet 28, by preventing the suture from entering the suture cleat 26. The pulley rod 32 also increases the strength of the anchor 10 by extending to the distal tip 46 of the anchor body 12 during initial deployment. The insertion tube 36, as well as the pulley rod 32, transmits the insertion force from a mallet to the anchor during initial deployment. Rotation of the proximal knob 44 actuates a mechanism that retracts the pulley rod 32 between initial and final deployment stages. The knob release slide 42 releases the knob 44 to allow for removal of the inserter 30 after final deployment. The suture cleat retainers 34 maintain a set gap in the suture cleat 26 during final deployment.

The remaining FIGS. 14-32 will now be referenced in connection with a description of methods of using the inventive system to deploy an anchor 10 in bone 48.

Figure 14:
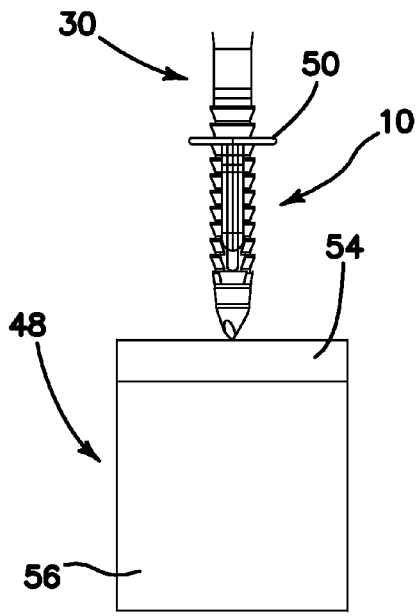
FIG. 14 is an elevational view illustrating a first step of a method of using the present invention.
Figure 15:
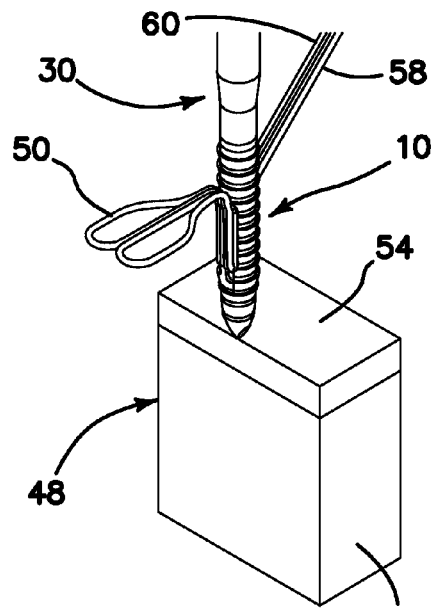
FIG. 15 is an isometric view showing the same step as that shown in FIG. 14.

To deploy the anchor 10 in a suitable bone site, suture 50 is first passed through soft tissue (not shown) requiring repair. Viewing, for example, FIG. 19, the suture loops 51 in the suture 50 would normally be occupied by the soft tissue to be approximated against the bone 48, but that tissue is not shown, for clarity. Alternatively, soft tissue itself may be anchored directly in place within the desired bone site 48, rather than using suture 50, in which case the tissue is manipulated in the same way as the suture to be described in this explanation. For this reason, though the term "suture" is used throughout this specification, for convenience, the term should be considered sufficiently broad to include other media having similar functional characteristics, including soft tissue itself. A pilot hole 52 (FIGS. 9 and 28) is drilled or punched into the attachment site (bone 48), through the cortical bone layer 54 and into the cancellous bone layer 56. In some circumstances, the optional metal distal tip 38 may be employed (FIG. 9), in which case the step of drilling a pilot hole is unnecessary. The suture is then fed through the suture eyelet 28, as shown in FIGS. 14 and 15, directly or with a snare. One or more suture ends 58, 60 (FIG. 15) may be placed through the eyelet 28.

Figure 16:
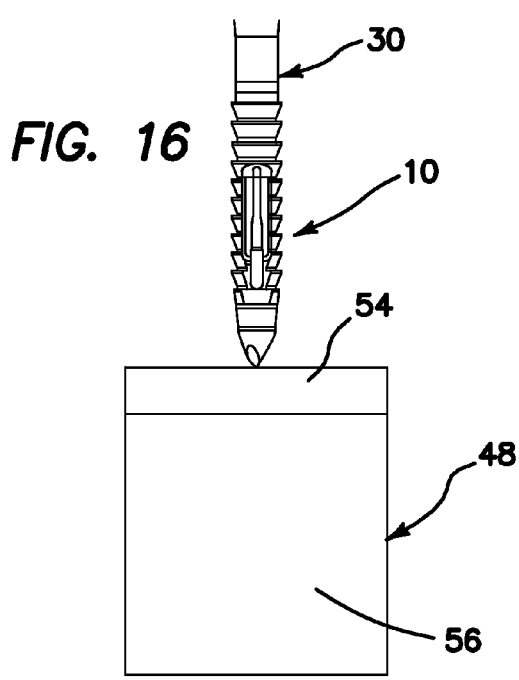
FIG. 16 is an elevational view similar to FIG. 14 with the suture removed for clarity.
Figure 17:
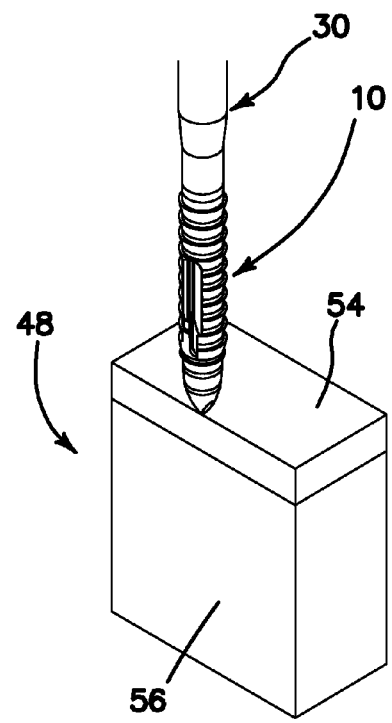
FIG. 17 is an isometric view similar to FIG. 15 with the suture removed for clarity.
Figure 18:
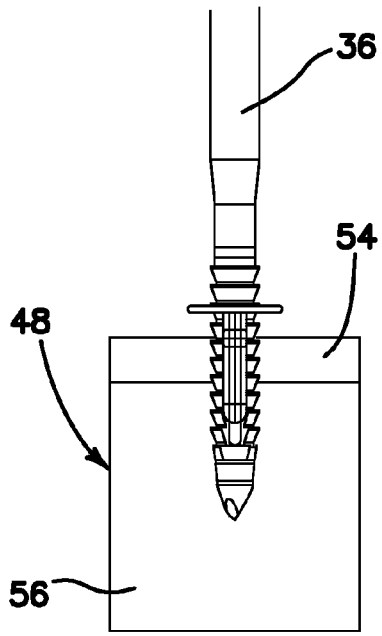
FIG. 18 is an elevational view showing a second step of the described inventive method.
Figure 19:
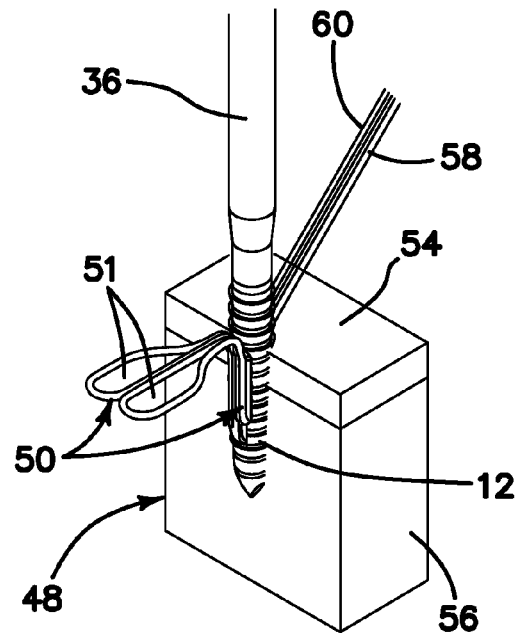
FIG. 19 is an isometric view of the step illustrated in FIG. 18.
Figure 20:
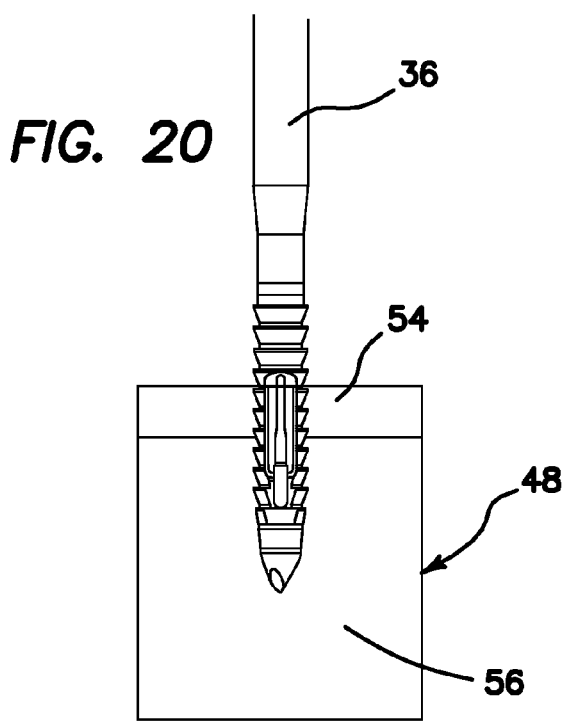
FIG. 20 is an elevational view similar to FIG. 18, with the suture removed for clarity.
Figure 21:
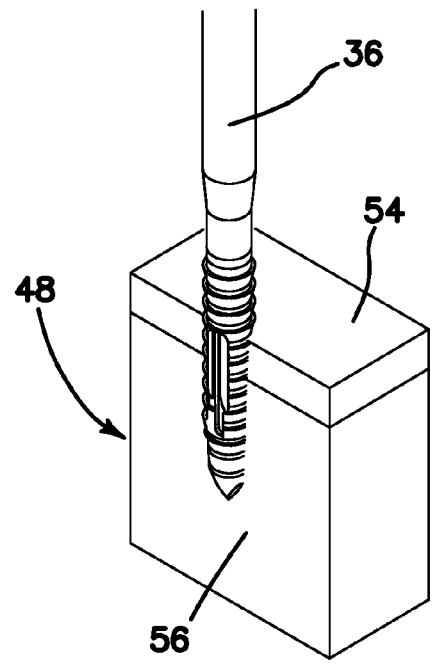
FIG. 21 is an isometric view similar to FIG. 19, with the suture removed for clarity.

With the anchor 10 and attached inserter 30 positioned at the desired bone site, as shown in FIGS. 14 and 15, initial deployment of the anchor 10 can occur. It should be noted that FIGS. 16 and 17, and FIG. 28, illustrate the same step as FIGS. 14 and 15, with the suture 50 removed for clarity. To initiate this initial deployment, a mallet is driven against the proximal end of the handle portion 40 to drive the anchor 10 distally to its initial deployment position, as shown in FIGS. 18 and 19, and also in FIGS. 20 and 21, and 29, with the suture again removed for clarity. At this juncture, the suture recess 18 is acting to apply pressure to the sutures or tissue 50 disposed between the outer surface of the anchor body 12 and the adjacent bone surface, as well as against the suture pinch ramp 24. This pressure maintains the tension on the suture 50.

The free suture ends 58, 60 may be individually tensioned around the suture pulley rod 32 to approximate the tissue within the suture loops 51 up against the anchor and repair site and its surrounding bone 48. If the suture is over-tensioned, a probe may be used to loosen the tissue side of the suture.

Once the desired tension is achieved, the suture pulley rod 32 is pulled proximally into the insertion tube 36, by rotating the threaded proximal knob 44 on the handle portion 40 until further rotation is prevented. When the tube 36 is retracted by the rotation of knob 44, the gap of the suture cleat 26 is exposed. At this point, the suture cleat retainers 34 are in position on either side of the suture cleat 26. This retracted pulley rod position is illustrated in FIGS. 26 and 27, which is the position required prior to the final insertion step. As noted above, the suture cleat 26 is exposed and held open by the suture cleat retainers 34, which thus allow the suture to pull into proper position during final insertion.

Figure 22:
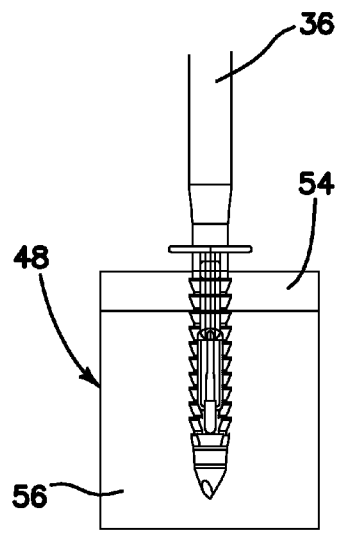
FIG. 22 is an elevational view showing a third step of the described inventive method.
Figure 23:
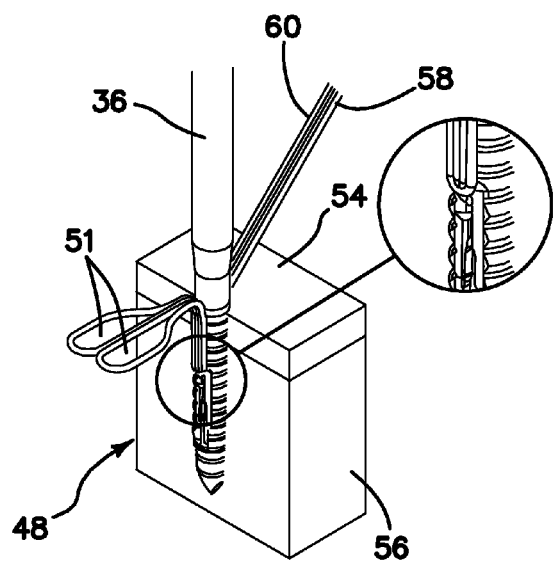
FIG. 23 is an isometric view of the step illustrated in FIG. 22.
Figure 24:
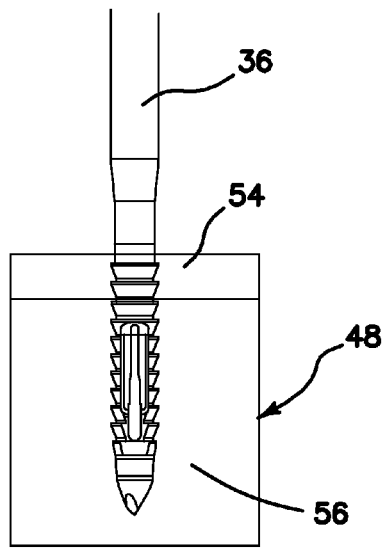
FIG. 24 is an elevational view similar to FIG. 22, with the suture removed for clarity.
Figure 25:
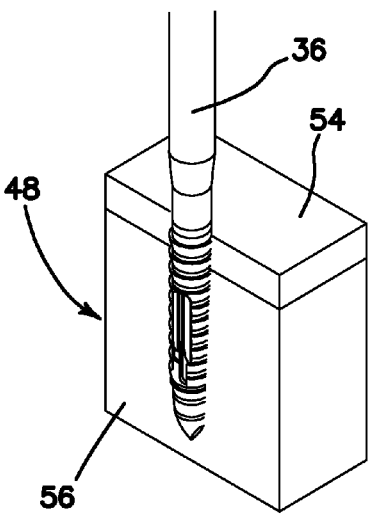
FIG. 25 is an isometric view similar to FIG. 23, with the suture removed for clarity.
Figure 30:
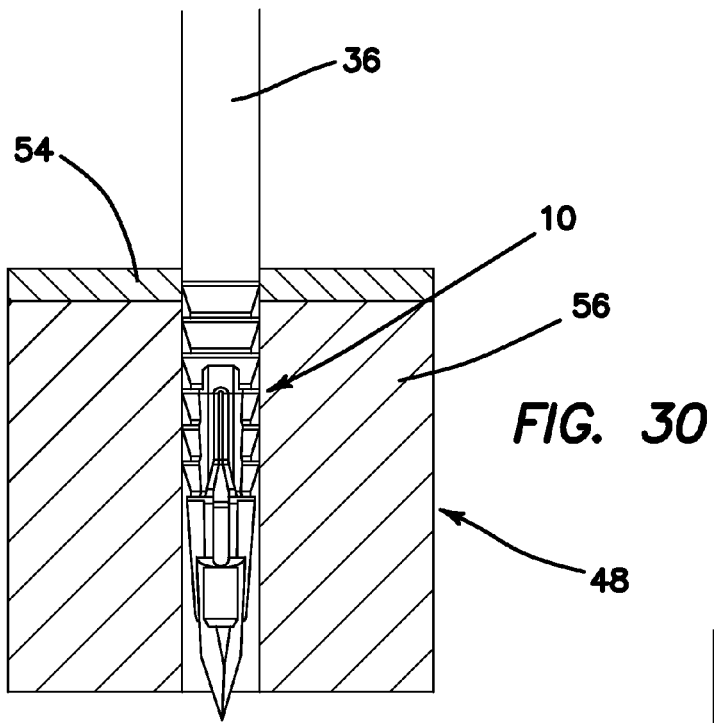
FIG. 30 is an elevational view similar to FIGS. 28 and 29, illustrating the third step of the inventive method which is also shown in FIGS. 22-25, with the suture removed for clarity.

At this juncture, the final deployment steps are initiated, as shown in FIGS. 22 and 23, and also in FIGS. 24 and 25, and 30, wherein the suture 50 has been removed for clarity. With the gap of the suture cleat 26 maintained by the suture cleat retainers 34, the inserter handle 40 is again malleted, directing insertion force into the insertion tube 36 until the anchor 10 rests below the surface of the bone, as shown in FIG. 30. Because the suture 50 has maintained an equal distance from the surface of the bone, post-tensioning and post-final deployment, the tension in the suture 50 is maintained. If additional tension is required, the anchor can be malleted deeper into the bone, pulling the suture ends with it, thereby increasing tension.

The suture 50 is now pinched between the suture barbs 14 and the bone on the tissue side of the anchor, as shown in FIG. 23. It is also pinched between the suture cleats 26 on both sides of the anchor body 12. Finally, the free suture ends 58, 60 are pinched between the suture barbs 14 and the bone opposite to the tissued side of the anchor.

Figure 31:
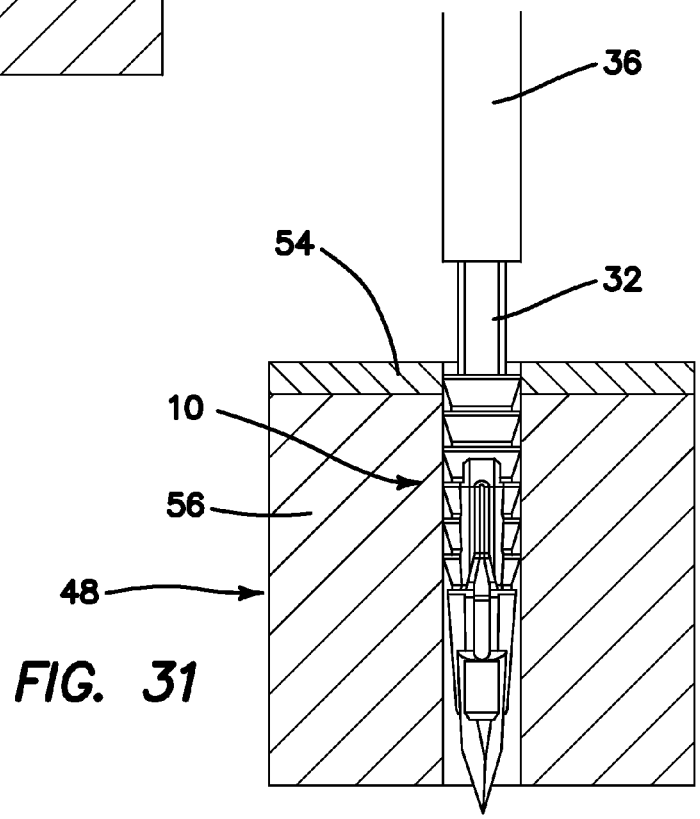
FIG. 31 is an elevational view similar to FIG. 30, showing the proximal withdrawal of the suture pulley rod in accordance with the method of the present invention.
Figure 32:
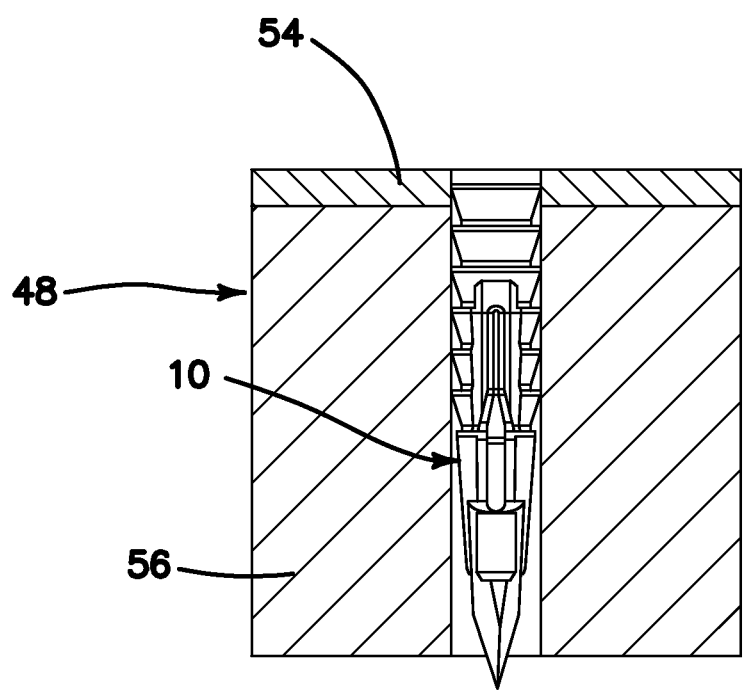
FIG. 32 is an elevational view similar to FIGS. 28-31, showing the final completed deployment of the inventive anchor.

The suture pulley rod 32 may now be pulled out of the anchor body 12, as shown in FIG. 31, releasing the inserter 30 by actuating the knob release slide 42 to allow the threaded knob 44 to be free to rotate. The knob 44 is then rotated until the inserter is released from the implant. At this juncture, the free suture ends can be cut, as shown in FIG. 32, which completes the repair.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. An anchoring system for securing tissue to bone, comprising
an implant comprising a body having a suture recess having a length extending along a portion of a length of the body, said recess having a predetermined depth below an outer surface of the body and being open to the outer surface of the body along the length of the recess; a suture pinch ramp disposed within the suture recess at the proximal end thereof, a suture cleat within the suture recess adjacent to the suture pinch ramp at the proximal end thereof, and a suture eyelet within the suture recess and extending transversely through a width of the body, the suture pinch ramp having a depth approximately equal to said predetermined depth at a distal end thereof and sloping outwardly in a proximal direction so that a depth of a proximal end of the suture pinch ramp approaches zero, the anchoring system further comprising bone displacement tabs disposed on a distal portion of the implant body, for displacing bone distal to suture to thereby allow optimal suture sliding during initial deployment of the anchor, the bone displacement tabs comprising protruding surfaces distal to the suture recess.

2. The anchoring system as recited in claim 1 wherein the implant further comprises external surface features for securing the implant within surrounding bone.

3. The anchoring system as recited in claim 2, wherein the external surface features comprise bone barbs.

4. The anchoring system as recited in claim 3, and further comprising suture barbs disposed on an outermost surface of the body at a proximal end thereof, for clamping suture or tissue between the outer surface of the body and adjacent bone, the suture barbs having a blunter outer profile than the bone barbs.

5. The anchoring system as recited in claim 1, and further comprising an inner cavity having an opening at a proximal end of the anchor body, for receiving an insertion device.

6. The anchoring system as recited in claim 1, and further comprising an insertion member which is engageable with said anchor body to deploy said anchor in bone.

7. The anchoring system as recited in claim 6, wherein said insertion member comprises a proximal handle portion and an insertion tube connected to a distal end of the handle portion.

8. The anchoring system as recited in claim 7, and further comprising a suture pulley rod extendable from and retractable into a distal end of the insertion tube.

9. The anchoring system as recited in claim 8, and further comprising a pair of cleat retainers on a distal end of the pulley rod, wherein a gap is disposed between the pair of cleat retainers.

10. The anchoring system as recited in claim 8, and further comprising a rotatable knob on said handle portion for retracting and extending the pulley rod relative to the insertion tube.

11. The anchoring system as recited in claim 10, and further comprising a knob release slide disposed on said handle.

* * * * *